Dec. 16, 1952 E. S. BOERNER Plant Pat. 1,155
ROSE PLANT
Filed Jan. 24, 1952
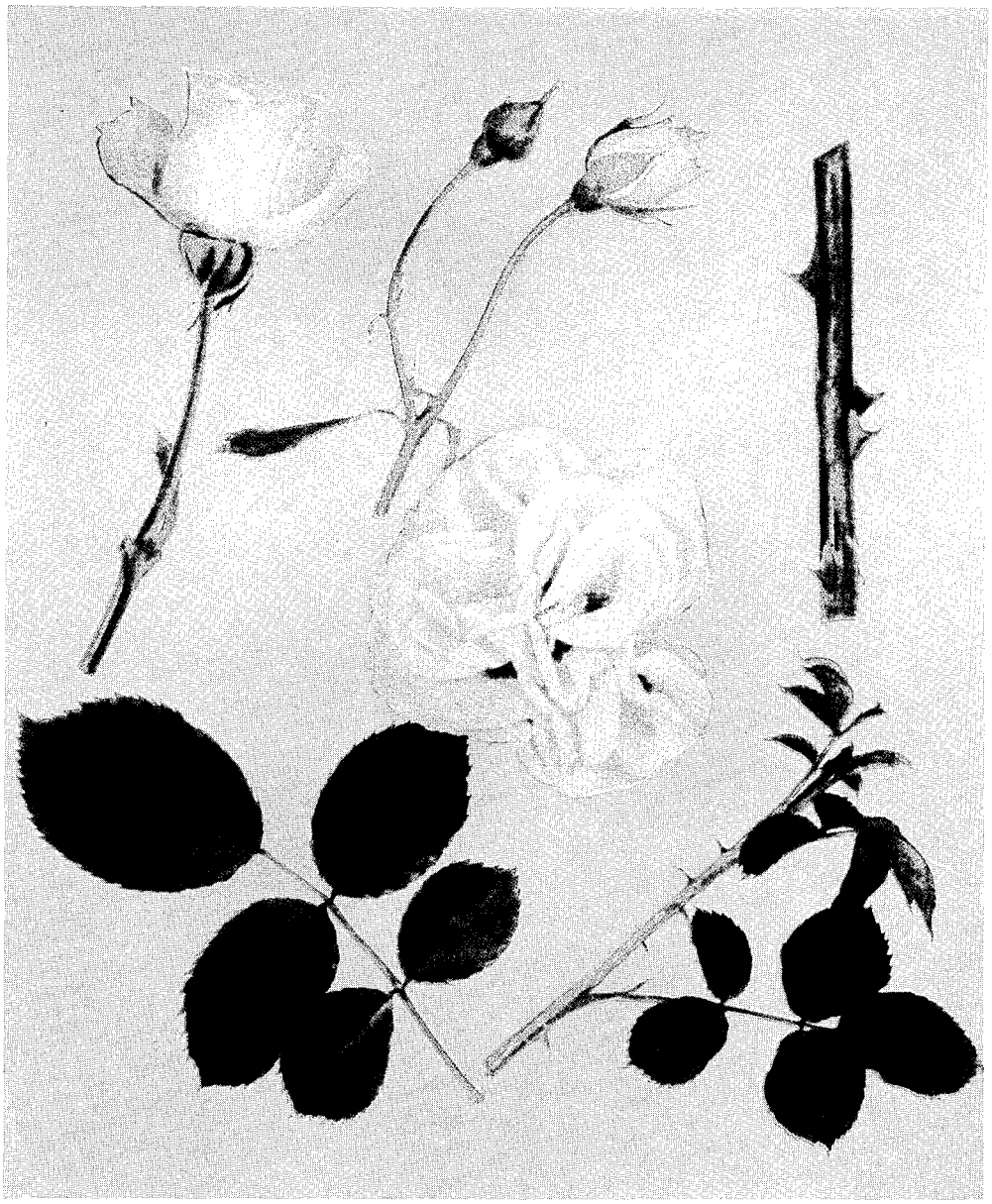
Inventor.
E. S. Boerner
By: Robb & Robb
Attorneys.

Patented Dec. 16, 1952

Plant Pat. 1,155

UNITED STATES PATENT OFFICE 1,155

ROSE PLANT

Eugene S. Boerner, Newark, N. Y., assignor to Jackson & Perkins Company, Newark, N. Y., a corporation of New York Application January 24, 1952, Serial No. 267,974

1 Claim. (Cl. 47—61)

The present invention relates to a new and distinct variety of rose plant of the large-flowered polyantha class, originated by me by crossing an unnamed and unpatented Terra Cotta seedling of "Pinocchio" (Plant Patent No. 484) with the variety "Fashion" (Plant Patent No. 789).

The primary objective in making this cross was to obtain a new variety of rose plant having larger-sized blooms in the range between Terra Cotta and Reddish-Orange color, with the same free-blooming habits of its parents. This objective was fully achieved, as evidenced by the fact that my new variety bears flowers from three to three and one-half inches in diameter, and remains substantially constantly in bloom throughout the growing season.

The new variety is still further distinguished from its parents, as well as from all other known varieties of its class, by the predominant Rose Doree color of its flowers, which are lightly overcast with Scarlet Red; by the long-lasting quality of the blooms both as cut flowers and on garden plants; and by the relatively stiff petals of its flowers.

Asexual reproduction of the new variety by budding at Newark, New York, and at Pleasanton, California, shows that the foregoing characteristics come true to form and are established and transmitted through succeeding propagations.

The accompanying drawing shows specimen flowers, foliage, stems and thorns of my new variety, with color terminology in accordance with Ridgway's Color Standards and Nomenclature:

Parentage: Seedling.

*Seed parent.*—An unnamed Terra Cotta seedling of "Pinocchio."

*Pollen Parent.*—"Fashion."

Classification:

*Botanic.*—Large-flowered polyantha.

*Commercial.*—"Fashion" type.

*Flower*

(Observations made in the greenhouse at Newark, New York, in the late morning in the latter part of the month of October.)

Blooming Habit: Recurrent—continuous.

Bud:

*Size.*—Medium.

*Form.*—Ovoid; is not affected by wet or hot weather.

*Color.*—When sepals first divide—Nopal Red, Plate 1. When petals begin to unfurl—Scarlet Red, Plate 1. When half blown—inside of petals; Begonia Rose, Plate 1, lightly overcast with Spectrum Red, Plate 1; reverse of petals: Scarlet Red, Plate 1.

*Sepals.*—Slightly branched; curl back when petals begin to unfurl. Color—inside: Biscay Green, Plate 17; outside: Lettuce Green, Plate 5.

*Calyx.*—Shape—pear. Size — small. Aspect—smooth. Odor when rubbed—none. Color—Lettuce Green, Plate 5.

*Peduncle.* — Length — medium. Aspect — rough. Strength—erect; slender. Color—Oil Green, Plate 5.

*Opening.*—Opens up well; is not affected by adverse weather conditions.

Bloom:

*Size.*—Medium. Average size when fully expanded—3 inches to 3½ inches.

*Borne.*—Singly and in pyramidal clusters.

*Stems.*—Medium size; normal strength.

*Form.*—When first open—cupped. Permanence—retains its form to the end.

*Petalage.*—Double (full but open center). Number of petals under normal conditions—20 to 25.

*Color.*—Center of flower—Rose Doree, Plate 1, lightly overcast with Scarlet Red, Plate 1. Outer petals—Begonia Rose, Plate 1, lightly overcast with Deep Rose Pink, Plate 12. Base of petals (aiglet)—Barium Yellow, Plate 16. Inside of petals—Rose Doree, Plate 1, lightly overcast with Scarlet Red, Plate 1. Reverse of petals—Rose Red, Plate 12, lightly overcast with Scarlet Red, Plate 1. General tonality from a distance Begonia Rose, Plate 1, overcast with Scarlet Red, Plate 1.

*Discoloration.*—General tonality at end of first day—Rose Doree, Plate 1, lightly overcast with Scarlet Red, Plate 1. Second day—Begonia Rose, Plate 1, lightly overcast with Rose Doree, Plate 1. Third day—Begonia Rose, Plate 1.

Petals:

*Texture.*—Thick; is not affected by wet or hot weather.

*Appearance.* — Inside — satiny; outside — shiny.

*Form.*—Oval.

*Arrangement.* — Imbricated (regularly arranged shingle-like). Petaloids in center—few; small.

*Persistance.*—Drop off cleanly.

*Fragrance.*—Slight. Nature — slight fruity (Russet apple).

*Lasting quality.*—On the plant and as cut flower—long.

*Genital organs*

Stamens, anthers:
*Size.*—Medium; many.
*Arrangement.*—Regular around styles.
*Color.*—Cadmium Yellow, Plate 3.
Stamens, filaments (threads):
*Length.*—Medium.
*Color.*—Picric Yellow, Plate 4.
Pollen: Color—Maryta Yellow, Plate 4.
Styles: Columnar; uneven and short length; thin.
Stigmas: Color—Sulphur Yellow, Plate 5.
Ovaries: All enclosed in calyx.

*Plant*

Form: Bush.
Growth: Vigorous; upright; irregular in form.
Foliage: 5 to 7 leaflets.
*Size.*—Medium.
*Quantity.*—Normal abundance.
*Color.*—New foliage—upper side: Yellowish Oil Green, Plate 5, with Oxblood Red, Plate 1, serrations; under side: Lettuce Green, Plate 5, with Oxblood Red, Plate 1, serrations. Old foliage—upper side: Cress Green, Plate 31; under side: Rainette Green, Plate 31.
*Shape.*—Oval, pointed.
*Texture.*—Upper side and under side—smooth. Ribs and veins—ordinary.
*Edge.*—Serrated (saw-toothed).
*Serration.*—Double; small.

*Leaf stem.*—Color—Absinthe Green, Plate 31. Under side—prickles.
*Stipules.*—Medium length; smooth.
Wood:
*New wood.*—Color — Cosse Green, Plate 5. Bark—smooth.
*Old wood.*—Color—Spinach Green, Plate 5. Bark—smooth.
Thorns:
*Thorns.*—Quantity—on main stalks from base and on laterals from stalk—ordinary. Form—flat base; medium length; hooked downward. Color when young—Eugenia Red, Plate 13. Position—irregular.
*Prickles.*—Quantity—on main stalks and on laterals—none.
*Short needles.*—On main stalks and on laterals—none.

I claim:

A new and distinct variety of rose plant of the large-flowered polyantha class, substantially as herein shown and described, characterized as to novelty particularly by its relatively large-size flowers which remain substantially constantly in bloom during the growing season, by the relative stiffness of the flower petals, by the dominant Rose Doree color, lightly overcast with Scarlet Red, of its flowers, and by the long-lasting quality of the flowers both as cut flowers and on garden plants.

EUGENE S. BOERNER.

No references cited.